United States Patent [19]

Sekutowski et al.

[11] Patent Number: 6,060,521

[45] Date of Patent: May 9, 2000

[54] AQUEOUS DISPERSION OF A PARTICULATE SOLID HAVING A HYDROPHOBIC SURFACE AND FILMS PRODUCED THEREBY

[75] Inventors: Dennis G. Sekutowski, Stockton, N.J.; Gary J. Puterka; David Michael Glenn, both of Shepherdstown, W. Va.

[73] Assignee: Engelhard Corporation United States Department of Agriculture, Iselin, N.J.

[21] Appl. No.: 09/182,583

[22] Filed: Oct. 29, 1998

Related U.S. Application Data

[63] Continuation of application No. 08/812,301, Mar. 5, 1997, Pat. No. 5,908,708.

[51] Int. Cl.$^7$ .............................. B01J 13/00; B05D 3/02; B05D 7/06; B27K 3/52
[52] U.S. Cl. ................. 516/79; 47/DIG. 11; 71/DIG. 1; 427/384; 427/393.4; 428/541; 516/77; 516/100
[58] Field of Search .................... 516/77, 79, 100

[56] References Cited

U.S. PATENT DOCUMENTS

| | | | |
|---|---|---|---|
| 2,441,423 | 5/1948 | Elliot et al. ................................ 260/29 |
| 2,733,160 | 1/1956 | Iler ............................................ 117/16 |
| 2,818,340 | 12/1957 | Goddin et al. ................................ 99/2 |
| 2,948,632 | 8/1960 | Albert et al. . | |
| 3,120,445 | 2/1964 | Aluisi et al. ............................. 106/286 |
| 3,124,505 | 3/1964 | Doyle et al. . | |
| 3,159,536 | 12/1964 | Marotta ..................................... 167/12 |
| 3,227,657 | 1/1966 | Haden et al. ............................. 252/317 |
| 3,235,451 | 2/1966 | Odeneal ..................................... 167/42 |
| 3,346,507 | 10/1967 | Taulli ....................................... 252/316 |
| 3,964,649 | 6/1976 | Alexander ................................ 222/399 |
| 4,071,374 | 1/1978 | Minton ................................. 516/101 X |
| 4,098,600 | 7/1978 | Chupp ........................................ 71/105 |
| 4,203,864 | 5/1980 | Sawyer, Jr. ................................ 516/79 |
| 4,274,883 | 6/1981 | Lumbeck et al. ........................ 106/308 |
| 4,279,895 | 7/1981 | Carle ......................................... 424/127 |
| 4,382,868 | 5/1983 | House ................................... 516/100 X |
| 4,632,936 | 12/1986 | Boase et al. ............................. 514/465 |
| 4,634,463 | 1/1987 | Ohsuga . | |
| 4,705,816 | 11/1987 | Pole ............................................ 43/52 |
| 5,122,518 | 6/1992 | Vrba ........................................... 514/63 |
| 5,186,935 | 2/1993 | Tucker ..................................... 424/410 |
| 5,392,559 | 2/1995 | Long ........................................... 43/52 |
| 5,393,461 | 2/1995 | Fillipova ................................. 252/314 |
| 5,414,954 | 5/1995 | Long ......................................... 43/121 |
| 5,455,220 | 10/1995 | Dedolph ................................. 504/241 |
| 5,480,638 | 1/1996 | Erwin ....................................... 424/614 |
| 5,656,571 | 8/1997 | Miller et al. ............................. 504/116 |

FOREIGN PATENT DOCUMENTS

| | | |
|---|---|---|
| 2005190 | 9/1970 | Germany . |
| 2926095 | 3/1980 | Germany . |
| 1792257A3 | 6/1990 | U.S.S.R. . |

*Primary Examiner*—Richard D. Lovering
*Attorney, Agent, or Firm*—Raymond F. Keller

[57] ABSTRACT

Aqueous dispersion of a particulate solid containing a low boiling organic liquid in which the particulate solid has a hydrophobic outer surface which is suitable for applying to a substrate to form a continuous hydrophobic film thereon.

8 Claims, No Drawings

AQUEOUS DISPERSION OF A PARTICULATE SOLID HAVING A HYDROPHOBIC SURFACE AND FILMS PRODUCED THEREBY

RELATED APPLICATIONS

This application is a continuation of patent application Ser. No. 08/812,301 filed Mar. 5, 1997 and now U.S. Pat. No. 5,908,708.

FIELD OF THE INVENTION

The present invention is directed to an aqueous dispersion of a particulate solid having a hydrophobic outer surface which is suitable for applying to a substrate to form a continuous hydrophobic film thereon. The film applications of the present invention include coating surfaces to make them water resistant.

BACKGROUND OF THE INVENTION

The prior art has recognized the utility of inert particulate solids as insecticides, see for example; Driggers, B. F., "Experiments with Talc and Other Dusts Used Against Recently Hatched Larvae of the Oriental and Codling Moths", *J. Econ. Ent.* 22 327–334 (1929); Hunt, C. R., "Toxicity of Insecticide Dust Diluents and Carriers to Larvae of the Mexican Bean Beetle", *J. Econ. Ent.* 40 215–219 (1947); and U.S. Pat. No. 3,159,536 (1964), each of which is incorporated herein by reference.

These references all describe applying particulate solids to foliage or insects by dry dusting. Although dry dusting is useful for laboratory experimentation it is not applicable for large scale agricultural use. The use of dry dusting has declined because the extremely fine particles, usually on the order of less than 30 um, with a median particle size typically between 0.5 to 3.0 um, are prone to drift and therefore have high negative environmental impact. Dry particles also do not adhere well to the target substrate (e.g. plants). Typically only 10% to 20% of the dry dust is deposited onto the target. (*Pesticide Application Methods* by G. A. Mathews Longman Scientific & Technical, Second Ed. (1992).)

It has also been determined that hydrophobic particulate solids can be applied to substrates as a liquid composition to form a hydrophilic coating. To this end, the particulate substances have been combined with a dispersant having a hydrophilic end and a lipophilic end and the same added to water to form an aqueous dispersion. The dispersant concentrates at an interphase between the hydrophobic substance and water with the lipophilic end of the dispersant positioned toward the hydrophobic substance and the hydrophilic end toward the water.

General classes of dispersants are divided into different groups by chemical functionality, e.g., cationic, anionic, amphoteric, nonionic. Typical examples of surfactants include soaps (carboxylate salts), sulfonates, sulfated alcohol ethoxylates, alkylphenol ethoxylates, carboxylic and polyoxyethylene esters, amines, imidazolines, and quaternary ammonium salts. Extensive lists containing hundreds of commercial dispersants are readily available (see McCutcheon's Emulsifiers & Detergents N. Amer Ed. (1995)).

The use of dispersants, however, causes the particulate hydrophobic substance to become hydrophilic and to retain this hydrophilic character after drying. Therefore, when such dispersions are placed on a substrate they will retain water. Water results in surface damage to many substrates including agricultural crops and other plants (disease), lumber (rot), concrete (freeze cracking), soil (erosion), textiles, solid chemicals such as fertilizers (leach), and the like. Accordingly, the use of dispersants for employing a dispersion of hydrophobic particulate solids for protecting surfaces has been problematical.

It would therefore be a significant advance in the art of applying hydrophobic particulate solids to a substrate to provide the substrate with a continuous film of the particulate solid while retaining a hydrophobic character. The resulting film would provide a substantial deterrent to damage due to water.

SUMMARY OF THE INVENTION

The present invention is generally directed to an aqueous dispersion and to continuous films formed from the same in which a particulate solid having at least a hydrophobic outer surface is formed as an aqueous dispersion, thereafter coated onto a substrate and formed into a continuous film while retaining its hydrophobic character.

In particular, the present invention is directed to an aqueous dispersion comprising:
  a) a particulate solid having a hydrophobic outer surface;
  b) an amount of a low boiling organic liquid sufficient to enable the particulate solid to form a dispersion in water and to retain the hydrophobic outer surface upon drying; and
  c) water.

In another aspect of the invention, there is provided a method of forming a hydrophobic continuous film on a substrate comprising:
  a) adding a particulate solid having a hydrophobic outer surface to an amount of a low boiling organic liquid sufficient to form a slurry;
  b) adding said slurry to water to form an aqueous dispersion of said particulate solid;
  c) applying said aqueous dispersion to the substrate;
  d) enabling the aqueous dispersion to dry whereby a hydrophobic continuous film of said particulate solid is formed on the substrate.

DETAILED DESCRIPTION OF THE INVENTION

The finely divided hydrophobic particulate solids of the invention may be hydrophobic in and of themselves, e.g., mineral talc, graphite, or may be solids that are rendered hydrophobic by application of an outer coating of a suitable hydrophobic wetting agent (e.g. the particulate solid has a non-hydrophobic core and a hydrophobic outer surface). Such agents are well known in the art and common examples include: chrome complexes such as Volvan® and Quilon® obtained from DuPont; organic titanates such as Tilcom® obtained from Tioxide Chemicals; organic zirconate or aluminate coupling agents obtained from Kenrich Petrochemical, Inc.; organofunctional silanes such as Silquest® products obtained from Witco or Prosil® products obtained from PCR; modified silicone fluids such as the DM-Fluids obtained from Shin Etsu; and fatty acids such as Hystrene® or Industrene® products obtained from Witco Corporation or Emersol® products obtained from Henkel Corporation (stearic acid and stearate salts are particularly effective fatty acids for rendering a particle surface hydrophobic).

Many types of finely divided particulate solids are pretreated with hydrophobic wetting agents to render their surfaces hydrophobic, so that the particles will wet out and disperse better in non-aqueous matrixes such as used in plastics, rubber, and organic coatings. Typical particulate solid materials that are commercially treated with hydrophobic agents include: minerals, such as calcium carbonate, mica, talc, kaolin, bentonites, clays, attapulgite, pyrophyllite, wollastonite, silica, feldspar, sand, quartz, chalk, limestone, precipitated calcium carbonate, diatomaceous earth and barytes; functional fillers such as microspheres (ceramic, glass and organic), aluminum trihydrate, pyrogenic silica, ceramic fibers and glass fibers; and pigments such as colorants or titanium dioxide. Examples of preferred commercial solid hydrophobic particulates that are available as an article of commerce from Engelhard Corporation, Iselin, N.J. are sold under the trademark Translink®.

The term "finely divided" when utilized herein means that the individual particles have a median particle size below about 10 microns and preferably below 3 microns as measured by standard sedigraphic or laser light scattering methods. Preferably, the particulate solid material has a particle size distribution wherein up to 90% of the particles have a particle size of under about 10 microns.

The low boiling organic liquids useful in the present invention preferably contain from 1 to 6 carbon atoms. The term "low boiling" as used herein shall mean organic liquids which have a boiling point generally no more than 100° C. These liquids enable the particulate solids to remain in finely divided form without significant agglomeration. Such low boiling organic liquids are exemplified by: alcohols such as methanol, ethanol. propanol, i-propanol, i-butanol, and the like, ketones such as acetone, methyl ethyl ketone and the like, and cyclic ethers such as ethylene oxide, propylene oxide and tetrahydrofuran. Combinations of the above-mentioned liquids can also be employed. Methanol is the preferred liquid.

The low boiling organic liquid is employed in an amount sufficient to form a dispersion of the solid particulate material. The amount of the low boiling organic liquid is typically up to about 30 volume percent of the aqueous dispersion, preferably from about 3 to 5 volume percent and most preferably from about 3.5 to 4.5 volume percent. The hydrophobic particulate solid is preferable added to the low boiling organic liquid to form a slurry and then the slurry is diluted with water to form the aqueous dispersion. The resulting slurry retains the particles in finely divided form wherein most of the particles are dispersed to a particle size of less than 10 microns.

The following examples are illustrative of embodiments of the invention and are not intended to limit the invention as encompassed by the claims forming part of the application.

EXAMPLE 1

Three gram quantities of a hydrophobic clay (Translink® 77 manufactured by Engelhard Corporation), were separately dispersed in 2, 4, 6, 8, and 10 milliliters of methanol, respectively. The samples were then diluted with deionized water to a total volume of 100 millimeters to yield a series of slurries containing 2, 4, 6, 8, and 10% by volume of methanol, respectively.

The methanol/water slurries were allowed to set for 24 hours before glass slides, surrounded with two sided adhesive tape, were dipped into the slurries. Hydrophobicity was determined by measuring the contact angle of the resulting dried particulate films prepared from the aqueous dispersions of hydrophobic particles. As used herein the static contact angle is the equilibrium angle measured between a liquid and a solid by drawing a tangent at the point of contact. A dynamic contact angle analyzer records both advancing and receding contact angles by the Wilhelmy technique as a glass slide or another surface is moved up and down through a liquid. The relationship between wetting force and contact angle is given by the modified Youngs equation shown below:

$$F = \gamma p \cos\theta$$

where F=wetting force; $\gamma$=liquid surface tension; and p=wetting perimeter

All measurements herein were made in water using either glass slides surrounded by adhesive tape or dual sided adhesive tape coated with particulate solids. Calibration of the water surface tension was made using a platinum plate.

An angle below 90 degrees is considered hydrophilic while an angle above 90 degrees is considered hydrophobic. The contact angles of the respective dried particle films were recorded with a Cahn DCA (Dynamic Contact Angle) instrument. The results are shown in the Table 1. All of the films formed in accordance with the present invention were hydrophobic and gave contact angles well above 90 degrees.

A control sample was prepared in the same manner as described above except that the methanol was omitted. Without the methanol, the hydrophobic clay floated on the water and would not wet out even with vigorous agitation.

EXAMPLE 2

Three gram quantities of Translink® 77, manufactured by Engelhard Corporation, was separately dispersed into 2, 4, 6, 8, and 10 milliliters of ethanol, respectively. The samples were then diluted with deionized water to a total volume of 100 milliliters to yield a series of slurries containing 2, 4, 6, 8, and 10% by volume of ethanol, respectively. Contact angle measurements were performed as described in Example 1. The results are shown in Table 1.

The contact angle for each of the ethanol containing slurries was well above 90°. Thus each of the samples produced in accordance with the present invention retained its hydrophobic character.

TABLE 1

| % ALCOHOL | EXAMPLE 1 CONTACT ANGLE METHANOL | EXAMPLE 2 CONTACT ANGLE ETHANOL |
| --- | --- | --- |
| 2 | 164° | 148° |
| 4 | 151° | 153° |
| 6 | 147° | 140° |
| 8 | 130° | 167° |
| 10 | 155° | 157° |

EXAMPLE 3

Translink® 77 was dispersed in ethanol and/or methanol-containing solutions as shown in Table 2 and then the samples were diluted with water to yield slurries containing 4% by volume of the ethanol/methanol mixture dispersion. Dried particle films were made from the dispersions at 1, 8, 24 hours and greater than 24 hours after the dispersions were prepared. The contact angle measurements were made as described in Example 1 and the results are shown in Table 2. As shown in Table 2 the contact angle for each of the slurries of the present invention was well above 90 degrees indicating that the dried particulate films were hydrophobic. The dispersions were also stable for over 24 hours.

TABLE 2

| % METHANOL | % ETHANOL | CONTACT ANGLE 1 HR. | CONTACT ANGLE 8 HRS. | CONTACT ANGLE 24 HRS. | CONTACT ANGLE >24 HRS. |
|---|---|---|---|---|---|
| 4 | 0 | 158° | 156° | 142° | 152° |
| 3 | 1 | 138° | 153° | 139° | 143° |
| 2 | 2 | 132° | 136° | 154° | 141° |
| 1 | 3 | 149° | 155° | 157° | 153° |
| 0 | 4 | 158° | 133° | 150° | 147° |

EXAMPLE 4

Four dispersions of each containing 4 grams of Translink® 77 were prepared in water under low shear mixing conditions. The first dispersion employed a 4% concentration of methanol as the dispersant. The second dispersion was prepared in the same manner except that methanol was replaced by four drops of an alkoxylated fatty amine (Ethomeen 0/12 sold by Akzo Nobel Chemicals, Inc.) The third dispersion was prepared in the same manner except that four drops of a tall oil hydroxy ethyl imidazoline (Monazoline T sold by MONA Industries, Inc.) was used as the dispersant. The fourth dispersion was prepared in the same manner except that four drops of a propylene oxide ethylene oxide block copolymer (Pluronic L-62 sold by BASF Corporation) was used.

The particle size distribution of the resulting slurries was measured and the results are shown in Table 3.

TABLE 3

| DISPERSANT | PARTICLE SIZE DISTRIBUTION | | |
|---|---|---|---|
| | <10% | <50% | <90% |
| Methanol | 0.92 | 3.0 | 9.1 |
| Ethomeen 0/12 | 2.0 | 7.3 | 114.0 |
| Monazoline T | 2.3 | 7.4 | 87.3 |
| Pluronic L-62 | 2.3 | 7.8 | 90.1 |

As shown in Table 3, the aqueous dispersion formed in accordance with the present invention exhibited much finer particles than the dispersions formed by typical dispersants used in the industry. For example up to 90% of the particles in the dispersion of the present invention had a particle size of 9.1 or less while the closest comparative samples showed a particle size of 87.3 for up to 90% of the particles.

Each of the dispersions described above was sprayed onto a coated glass slide and allowed to dry. Thereafter, a drop of water was placed onto the coated glass slides. The droplet on the coated glass slide in accordance with the present invention remained beaded and did not spread out indicating that the coating was hydrophobic. Each of the water droplets on the other glass slides spread out indicating that the particle films were hydrophilic.

EXAMPLE 5

Four slurries were prepared as in Example 4 except that the slurries were made under high shear conditions. In particular, the slurries were milled for 30 minutes using a Cowles high-shear blade on a Premier Mill Corporation high speed dispersator. Particle size measurements were made of the slurries and the remainder of the slurries were filtered. Contact angle measurements of the dry particles were made. The results are shown in Table 4.

TABLE 4

| DISPERSANT | MEDIAN PARTICLE SIZE (MICRONS) | CONTACT ANGLE |
|---|---|---|
| Methanol | 2.1 | 160.0 |
| Ethomeen 0/12 | 37.0 | 76.0 |
| Monazoine T | 62.2 | 53.5 |
| Pluronic L-62 | 3.3 | 48.3 |

As shown from the results in Table 4, many of the agglomerates were broken down under high shear conditions. However, the particles were no longer hydrophobic except for the sample employing methanol.

EXAMPLE 6

The following example demonstrates the invention in an agricultural field application. In a plastic pail 100 pounds of Translink® 77 was slowly added to 16 gallons of commercial methanol under gentle agitation with a paddle. The mixture was then transferred to a recirculating spray tank and diluted to 400 gallons with water to make a slurry of 3% Translink®77 and 4% methanol in water. After five (5) minutes of mixing, the dispersion was ready to spray. A peach and apple orchard was sprayed using a Friendly® hydraulic sprayer fitted with standard fan nozzles. After spraying, the sprayed tree leaves were determined upon drying to be hydrophobic, since added water droplets were observed to bead up on the surfaces of the leaves.

EXAMPLE 7

Example 6 was repeated except that methanol was replaced with a 1% Safer® Soap (sold by Safer, Incorporated) which is a potassium fatty acid commonly used as an agricultural surfactant and insecticide. The orchards were sprayed as described in Example 6. Upon drying, the tree leaves were observed to be hydrophilic since added drops of water spread out upon the surfaces of the leaves.

What is claimed is:

1. An aqueous dispersion comprising:

a particulate solid material having a hydrophobic outer surface, the particulate solid material selected from the group consisting of calcium carbonate, kaolin, and pyrophyllite;

up to about 30% by volume of an alcohol enabling said particulate solid material to form a dispersion in water and to retain the hydrophobic outer surface upon drying; and water.

2. The aqueous dispersion of claim 1, wherein the particulate solid material has a mean particle size below about 3 microns.

3. The aqueous dispersion of claim 1, wherein up to 90% of the particulate solid material has a mean particle size below about 10 microns.

4. The aqueous dispersion of claim 1, wherein the particulate solid material comprises a non-hydrophobic core and a hydrophobic outer surface.

5. An aqueous dispersion comprising:

a particulate solid material having a hydrophobic outer surface, the particulate solid material comprising kaolin;

up to about 30% by volume of an alcohol enabling said particulate solid material to form a dispersion in water and to retain the hydrophobic outer surface upon drying; and water.

6. The aqueous dispersion of claim 5, wherein the particulate solid material has a mean particle size below about 3 microns.

7. The aqueous dispersion of claim 5, wherein up to 90% of the particulate solid material has a mean particle size below about 10 microns.

8. The aqueous dispersion of claim 5, wherein the particulate solid material comprises a non-hydrophobic core and a hydrophobic outer surface.

* * * * *